US008886299B2

(12) United States Patent
Yazicioglu et al.

(10) Patent No.: US 8,886,299 B2
(45) Date of Patent: Nov. 11, 2014

(54) SYSTEM AND METHOD FOR THE ANALYSIS OF ELECTROCARDIOGRAM SIGNALS

(71) Applicant: IMEC, Leuven (BE)

(72) Inventors: Refet Firat Yazicioglu, Leuven (BE); Tom Torfs, Kraainem (BE); Sachin Shrestha, Leuven (BE)

(73) Assignee: IMEC, Leuven (BE)

( * ) Notice: Subject to any disclaimer, the term of this patent is extended or adjusted under 35 U.S.C. 154(b) by 238 days.

(21) Appl. No.: 13/666,167

(22) Filed: Nov. 1, 2012

(65) Prior Publication Data

US 2013/0116588 A1     May 9, 2013

Related U.S. Application Data

(60) Provisional application No. 61/555,321, filed on Nov. 3, 2011.

(51) Int. Cl.
*A61B 5/04*           (2006.01)
*A61B 5/00*           (2006.01)
*A61B 5/0456*     (2006.01)

(52) U.S. Cl.
CPC .............. *A61B 5/726* (2013.01); *A61B 5/04017* (2013.01); *A61B 5/0456* (2013.01)
USPC .......................................... 600/516; 600/517

(58) Field of Classification Search
CPC ........................... A61B 5/0468; A61B 5/0472
USPC .................................................. 600/516, 517
See application file for complete search history.

(56) References Cited

U.S. PATENT DOCUMENTS

2009/0082684 A1*   3/2009   Sornmo et al. ................ 600/513
2009/0137916 A1*   5/2009   Maison-Blanche et al. .. 600/516

FOREIGN PATENT DOCUMENTS

CN           101828917 B      9/2011
EP            2298164 A2       3/2011

OTHER PUBLICATIONS

European Search Report, European Patent Application No. 12190865.1 dated Apr. 4, 2013.
Kim, Hyejung et al., "A Mixed Signal ECG Processing Platform With an Adaptive Sampling ADC for Portable Monitoring Applications", 33rd Annual International Conference of the IEEE EMBS, Boston, Massachusetts, US, Aug. 30-Sep. 3, 2011, pp. 2196-2199.

(Continued)

*Primary Examiner* — Christopher D Koharski
*Assistant Examiner* — Natasha Patel
(74) *Attorney, Agent, or Firm* — McDonnell Boehnen Hulbert & Berghoff LLP

(57) ABSTRACT

A microprocessor configured to receive and process digitized signals derived from an analogue ECG signal is provided. An example microprocessor comprises a beat detection unit configured to receive the in-phase and quadrature phase band power signals, calculate a band power value and an adaptive threshold value, and compare said band power value with said adaptive threshold value to detect a QRS complex of the ECG signal indicative of a detected valid beat; and an R peak detection unit configured to receive the digital ECG signal and information about the detected valid beat, select a portion of the received ECG signal as a first time window around the detected valid beat; determine the location of a first R peak position; and perform a time domain search in a second time window around said first R peak position in order to refine the location of an R peak position.

15 Claims, 4 Drawing Sheets

(56) References Cited

OTHER PUBLICATIONS

Torfs, T. et al., "Ultra Low Power Wireless ECG System with Beat Detection and Real Time Impedance Measurement", Proceeding of the IEEE Biomedical Circuits and Systems Conference (BioCAS), 2010, pp. 33-36, Nov. 2010.

Romero, I. et al., "Low Power Robust Beat Detection in Ambulatory Cardiac Monitoring", Proceedings of the IEEE Biomedical Circuits and Systems Conference (BioCAS) 2009, pp. 249-252, Nov. 2009.

\* cited by examiner

SYSTEM AND METHOD FOR THE ANALYSIS OF ELECTROCARDIOGRAM SIGNALS

CROSS-REFERENCE TO RELATED APPLICATIONS

This application claims priority under 35 U.S.C. §119(e) to U.S. Provisional Patent Application Ser. No. 61/555,321, filed on Nov. 3, 2011, and entitled "Method and System for Evaluating and Detecting Dynamically Changing Biopotential Electrical Signals", the full disclosure of which is incorporated herein by reference.

BACKGROUND

1. Technical Field

The present disclosure is related to a system and method for the analysis of electrocardiogram (ECG) signals and more particularly to the detection and location of the R peaks of an input ECG signal.

2. Technical Background

Monitoring of biopotential electrical signals is currently used in many applications. For example, ambulatory monitoring of an electrocardiogram (ECG) taken from a biological subject (patient) can be used to evaluate the heart condition of a patient, like ischemia, late potentials, heart rate variability etc. This is normally performed by measuring the patient's cardiac rhythm over an extended period of time to determine the regularity of the heart beat received. The biopotential electrical signals are measured during normal activity of the monitoring biological subjects, including any physical and psychological changes. This approach allows the evaluation of dynamically changing cardiac electrical phenomena that are often transient and of brief duration. Any abnormalities detected at this stage may indicate the existence of a heart condition, such as arrhythmia, which can be fatal and requires continuous monitoring to ensure the occurrence of the faster, slower or irregular heart rhythms. In this case, accuracy in detecting such abnormalities is of paramount importance since a wrong reading of the data received can compromise the life of the patient. Currently, there is a need for the development of battery powered portable systems that are small enough to be worn or carried comfortably by the patient without affecting his day to day activities.

The basic requirements of such portable, battery-powered systems are low power consumption and high accuracy in the detection of anomalies. The design will need to meet different specification compared to that of the hospitalized monitoring systems. This is due to the embedded algorithms required in such portable systems. The algorithm must satisfy the memory and computational complexity constraints of low powered embedded systems. Besides these constraints, an additional challenge for the embedded algorithms in portable systems is the extraction of information from noisy signals. The noise and motion artifacts of the biopotential signals measured by a portable system is of a higher order compared to those added to the biopotential signal measured in a controlled environment, for example in hospitalized monitoring. At the same time the need for accuracy and reliability remains high since it concerns the human health.

Known techniques presented in the state-of-the-art require at least high computational complexity and as a result most of them are not applicable in a low power embedded application.

A know solution that is applicable for ambulatory and low-power applications is described in patent application EP 2 298 164 A2, and mainly used for the calculation of the average heart bit rate (HBR). A problem with this solution though is that it is not accurate and reliable enough to be applied for the calculation of the heart bit rate variability (HBRV).

SUMMARY OF THE DISCLOSURE

According to an exemplary embodiment of the present disclosure there is provided a microprocessor configured to receive and process digitized signals derived from an analogue ECG signal, said digitized signals being a digital ECG signal and digital in-phase and quadrature phase band power signals, the microprocessor comprising: a beat detection unit configured to receive the in-phase and quadrature phase band power signals, calculate a band power value and an adaptive threshold value, and compare said band power value with said adaptive threshold value to detect a QRS complex of the ECG signal indicative of a detected valid beat; and an R peak detection unit configured to receive the digital ECG signal and information about the detected valid beat, select a portion of the received ECG signal as a first time window around the detected valid beat; determine the location of a first R peak position based on a continuous wavelet transform calculation of said selected portion of the received ECG signal; and perform a time domain search in a second time window around said first R peak position in order to locate a final R peak position. The first time window may be, for example, 140 milliseconds. The second time window may be, for example, 20 milliseconds.

According to an example embodiment, the beat detection unit is further configured to measure the time period in which the band power value exceeds the adaptive threshold value, and, in case said measured time period is equal or greater than a first period of time, indicating said detected QRS complex as a valid beat, or in case said measured time period is less than the first period of time, said detected QRS complex is not considered as a valid beat and is stored in a memory. The first period of time may be, for example, 32 milliseconds.

According to still another example embodiment, in case the beat detection unit does not detect, since the last detected valid beat, the occurrence of a new valid beat within a second period of time, it determines one, from a plurality of stored QRS complex, with the highest band power during the period and indicates said QRS complex as the valid beat. The second period of time may be, for example, the average beat duration time plus an additional amount of time, such as, for example, plus 200 milliseconds.

According to another example embodiment, in case the beat detection unit does not detect, since the last detected valid beat, the occurrence of a new valid beat within a third period of time, it recalculates the adaptive threshold value. The third period of time may be, for example, 4 seconds.

According to another example embodiment, the adaptive threshold value used to detect the QRS complex of the ECG signal may be defined based on the 1 Hz low pass-filtered version of the calculated band power value, limited to a minimum value of 18% of the peak value, and calculated as a moving average of a certain number of previously calculated thresholds.

According to another example embodiment, the continuous wavelet transform calculation may be a unit scale continuous wavelet transform calculation, which advantageously requires less computational complexity.

According to still another example embodiment, the R peak detection unit is configured to determine the location of the first R peak position by determining, after a boundary removal of a fourth time period, the coefficient with maximum value of the continuous wavelet transform calculation of said selected portion of the received ECG signal, and comparing said coefficient with a certain percentage of the mean of previously calculated maximum coefficient values. The fourth time period may be, for example, 10 milliseconds and said certain percentage of the mean of previously calculated maximum coefficient values may be, for example, 30%.

The disclosure also relates, in another example embodiment, to a system for the analysis of ECG signals comprising: an analog signal processing circuit including an electrocardiogram readout channel unit configured to generate a digital version of an ECG signal derived from a received analogue ECG signal; and a band power extraction channel unit configured to generate digital in-phase and quadrature phase band power signals derived from the received analogue ECG signal; and a microprocessor configured to receive and process signals provided by the analog signal processing circuit according to any of the embodiments of the disclosure.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

The disclosure will be further elucidated by means of the following description and the appended figures. Various exemplary embodiments are described herein with reference to the following figures, wherein like numerals denote like entities. The figures described are schematic and are non-limiting. Further, any reference signs in the claims shall not be construed as limiting the scope of the present disclosure. Still further, in the different figures, the same reference signs refer to the same or analogous elements.

DETAILED DESCRIPTION

Figure 1:
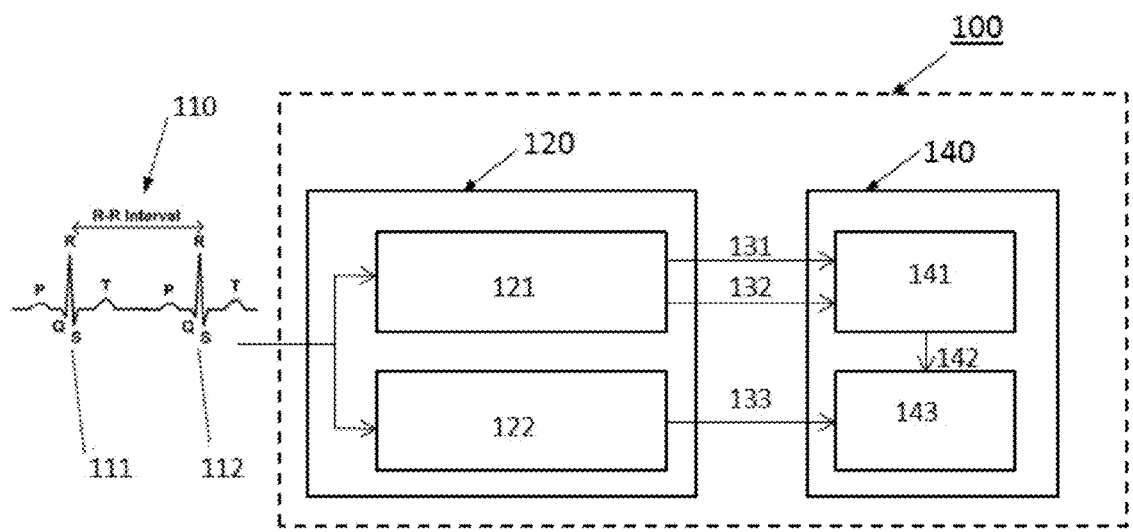
FIG. 1 shows a simplified block diagram of an exemplary embodiment of a system for analysis of ECG signals, according to an example of the present disclosure.

FIG. 1 shows a simplified block diagram of an exemplary embodiment of a system 100 for the analysis of an input analogue ECG signal 110, with the presence of a successive QRS complex 111 and 112. The system 100 comprises an analogue signal processing circuit 120 or front end and a microprocessor 140 adapted to receive and process signals provided by the analog signal processing circuit 120. The analogue signal processing circuit 120 comprises an electrocardiogram readout channel unit 122 adapted to generate a digital ECG signal version 133 derived from the received analogue ECG signal 110; and a band power extraction channel unit 121 adapted to generate digital in-phase 131 and quadrature phase 132 band power signal components derived from the received analogue ECG signal 110. The microprocessor 140 comprises a beat detection unit 141, providing a valid beat detection signal 142, and an R peak detection unit 143. It is understood that the functions of the microprocessor 140 herein described, according to the example embodiments of the disclosure, may take the form and be implemented in for example a low power microcontroller or digital signal processor or any other multi-purpose integrated circuit comprising a processing capability and memory.

The analogue signal processing (ASP) circuit 120 may be an application-specific integrated circuit (ASIC) which is advantageously used for monitoring ECG signals and provides reduced power consumption.

Figure 2:
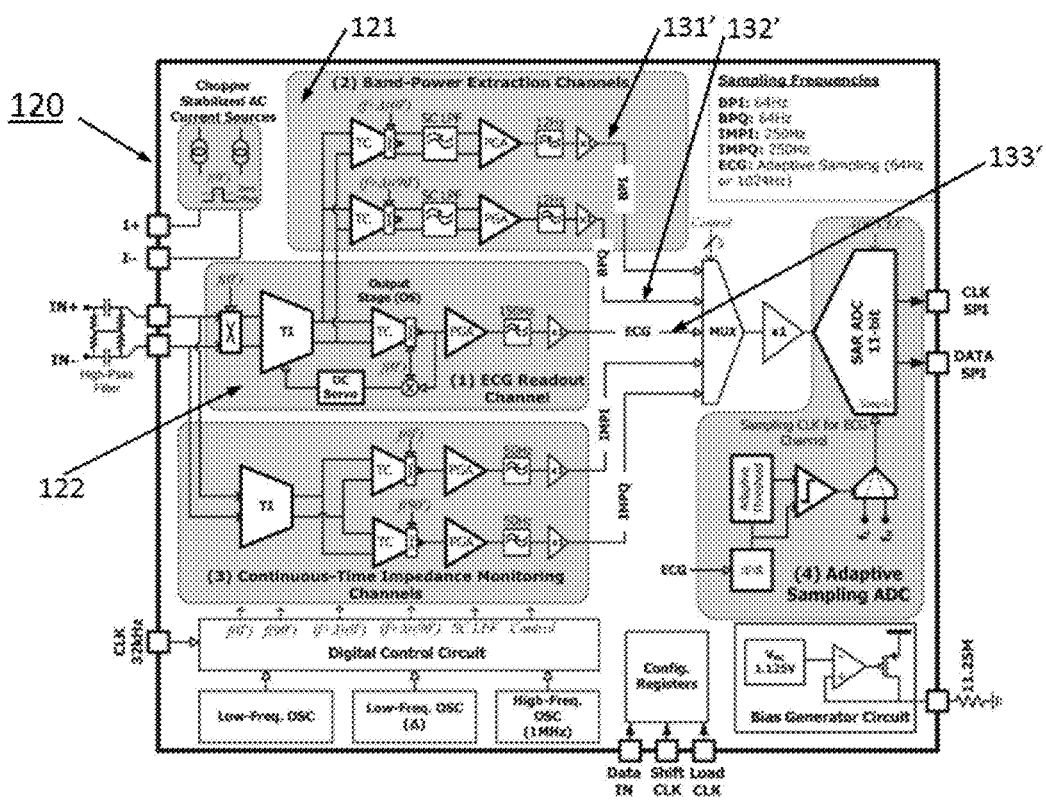
FIG. 2 illustrates a block diagram of an exemplary analogue signal processing circuit that can be used in the system for analysis of ECG signals, according to an example of the present disclosure.

An exemplary ASP ASIC 120 according to an example embodiment of the disclosure is shown in FIG. 2, comprising the electrocardiogram readout channel unit 122 and the band power extraction channel unit 121. The digital ECG signal 133, the digital in-phase band power signal component 131 and the digital quadrature phase band power signal component 132 are derived from their corresponding signal versions 133', 131' and 132' respectively in the ASP ASIC.

According to an example embodiment the ASP ASIC performs the functions of: ECG signal extraction with high resolution using ECG readout channel, feature extraction using a band-power extraction channel, adaptive sampling the ECG signals using an adaptive sampling analogue-to-digital converter, and impedance monitoring for signal integrity using an impedance monitoring channel. These functions enable, for example, the development of wireless ECG monitoring systems that have significantly lower power consumption but are more efficient that predecessor systems. The ASP ASIC may consume, for example, 30 µW from a 2V supply with compression provided by adaptive sampling providing large reductions in power consumption of a wireless ECG monitoring system of which the ASP ASIC forms a part. The ASP ASIC contains a high-performance instrumentation amplifier to amplify the ECG signal as well as a built-in analog-to-digital converter. It also features power efficient configurable analog band pass filters that output in-phase and quadrature components. The parameters of these filters have been modified in order to obtain optimal detection of the R peak over the MIT-BIH database. Through its configuration registers, the ASIC is programmed to provide band power output signal in the frequency band of 16 Hz±1.58 Hz. The sample rate of the ECG channel is 512 Hz and of the band power channels is 64 Hz per channel.

Figure 3:
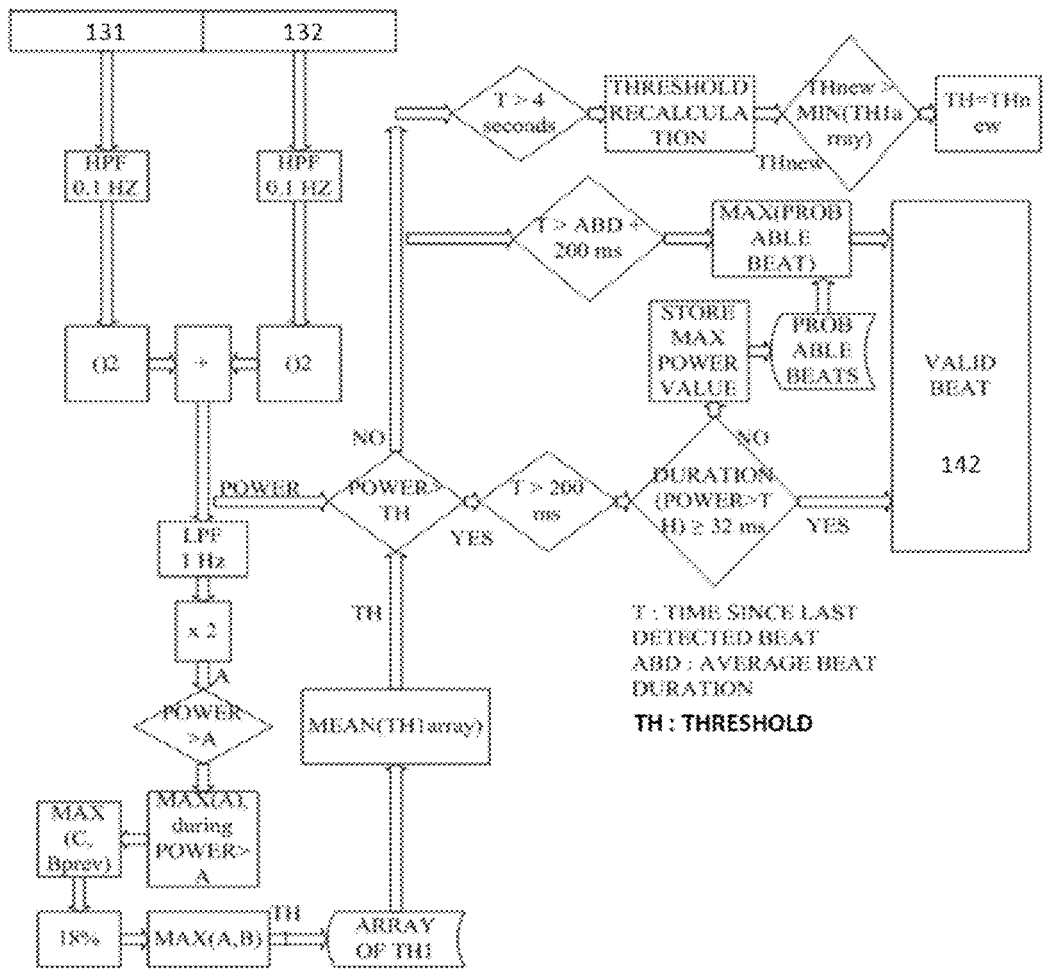
FIG. 3 illustrates a flow diagram of an exemplary implementation of the valid beat calculation, according to an example of the present disclosure.

FIG. 3 illustrates a flow diagram of an exemplary implementation of the valid beat calculation and detection performed in the beat detection unit 141 in order to provide an indication of a detected valid beat 142 to the R peak detection unit 143.

A known flow diagram for the detection of a valid beat is disclosed in published paper "*Ultra low power wireless ECG system with beat detection and real time impedance measurement*"; T. Torfs, R.F. Yazicioglu, S. Kim, H. Kim, C. Van Hoof, D. Buxi, I. Romero, J. Wijsman, F. Masse, J. Penders; Proceeding of the IEEE Biomedical Circuits and Systems Conference (BioCAS), 2010, pp. 33-36, November 2010. But as will be understood by the person skilled in the art, the prior art solution lacks the accuracy and reliability needed for an improved R peak location technique.

The beat detection unit 141 uses the magnitude of the in phase and quadrature band power signals 131 and 132, obtained, for example, from the band power extraction channel unit 121 of the analog signal processing circuit 120, to calculate a total band power of the ECG signal as the summation of the squares of it (after DC removal). An adaptive threshold is defined based on the 1 Hz low pass filtered version of the band power, limited to a minimum value of 18% of the peak value. The minimum value is adapted as the moving average of the last, for example eight (8), minimum thresholds being calculated. The calculated band power is compared to the adaptive threshold to indicate the presence of a beat. In order to determine whether a detected beat is valid, the duration for which the band power exceeds the adaptive threshold is measured. If the threshold crossing is too short, the beat is not immediately considered a valid beat but is stored. Later, if there is no occurrence of a valid beat within the average beat duration plus some additional time, the stored beat that exhibits the highest band power during the period is defined as the valid beat. The beat detection unit 141 also keeps track of the non-occurrence of beats, and if there are no beats detected, the adaptive threshold is recalculated and compared with the least value of stored thresholds to check if it can be defined as the new threshold. Such added additional constraints, based on the time duration, increase the resistance of the algorithm to the noise.

It shall be understood that the flow diagram of FIG. 3 and in the same manner the beat detection unit 141 may be implemented in software and/or hardware.

According to an example embodiment, the beat detection unit 141 takes advantage of the band power extraction features of a dedicated analog signal processing application-specific integrated circuit (ASP ASIC).

Figure 4:
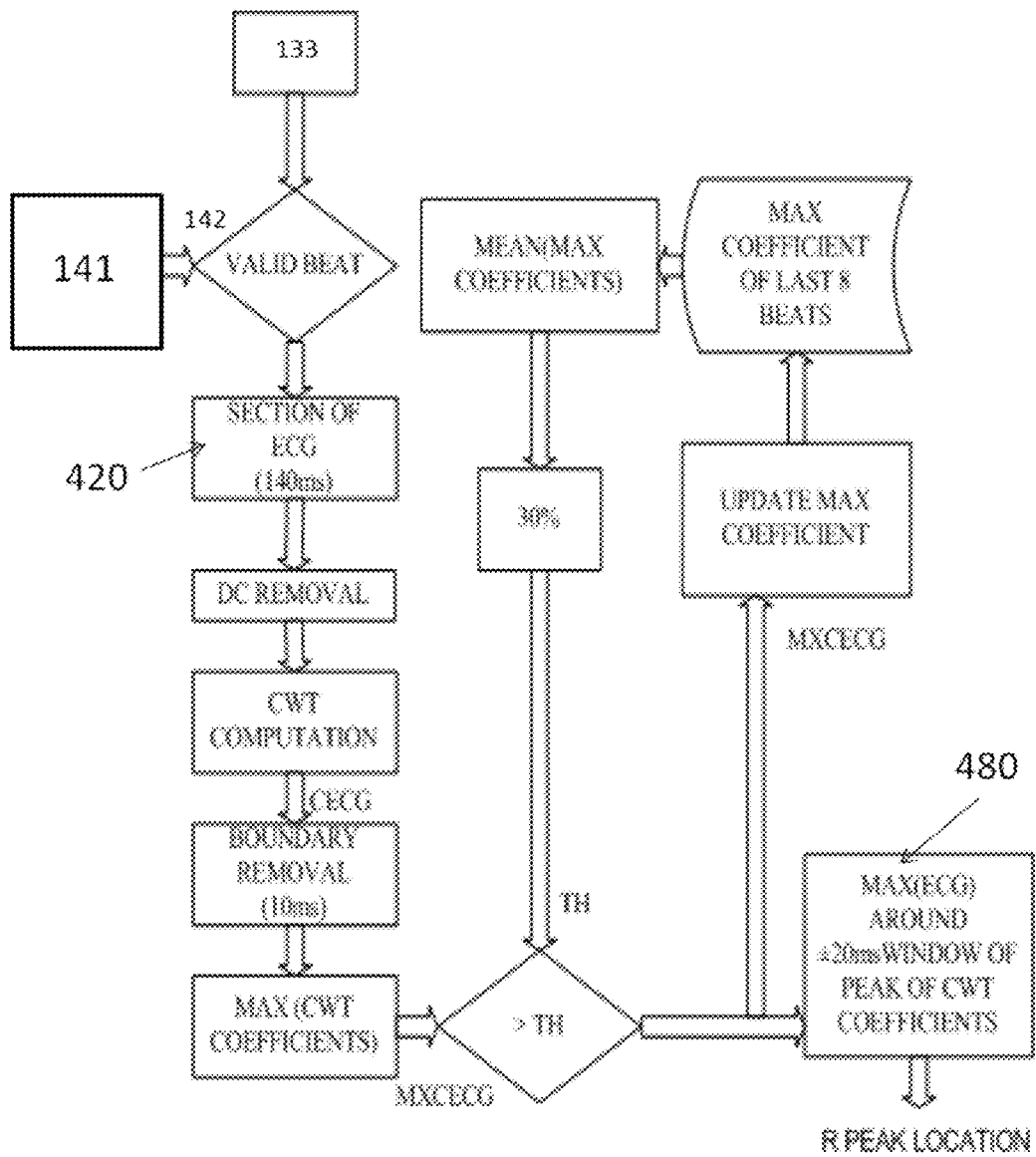
FIG. 4 shows a flow diagram of an exemplary implementation of the R peak detection and location, according to an example of the present disclosure.

FIG. 4 shows a flow diagram of an exemplary implementation of the R peak detection and location performed by the R peak detection unit 143.

It shall be noted that in order to locate the R peak after detection of a valid beat 142, the most straightforward approach would be to search in the time domain for the maximum absolute value after DC removal, in a certain window around the detected beat. However, this approach would lead to inaccuracies in cases where the architecture of the ASIC uses an equivalent of a 1st order low pass filter for the band power extraction. Due to the non-linear characteristics of this filter, a large variation in the delay, between the R peak and band power peak results, in the range of hundreds of milliseconds; this would lead to the need to make a time domain search over a larger interval. However, the larger the search window, the larger the possibility of false detection of the R peak becomes in the presence of artifacts.

According to an example embodiment of the disclosure, the R peak detection unit 143 performs the R peak search using a continuous wavelet transform calculation (CWT). A known continuous wavelet transform calculation (CWT) used for ECG signal beat detection is described in *"Low power robust beat detection in ambulatory cardiac monitoring"*; I. Romero, B. Grundlehner, J. Penders, J. Huisken, Y.H. Yassin; Proceedings of the IEEE Biomedical Circuits and Systems Conference (BioCAS) 2009, pp. 249-252, November 2009, which performs the CWT over blocks of 3 seconds overlapping 0.5 seconds on each side.

According to an example embodiment of the disclosure, the CWT computation is performed on a window of an ECG section (after DC removal) around the detected beat. Said window may be, for example, of 140 ms. The maximum CWT coefficient is evaluated after a boundary removal of 10 ms. This maximum value is compared with the 30% of the mean of previous maximum coefficient values, to determine its validity as correct R peak. Finally a time domain search in a narrow window of 20 ms is performed around this maximum position to refine the R peak location.

It shall be understood that the flow diagram of FIG. 4 and in the same manner the R peak detection unit 143 may be implemented with software and/or hardware means.

Further example embodiments and advantages of the disclosure may be described hereunder.

A proposed technique according to an example embodiment of the disclosure makes use of the dedicated ASIC for the band power measurement which advantageously greatly reduces the power consumption of the overall system.

According to another example embodiment, the CWT computation around the detected valid beat aids in the precise detection of the R peak and hence improving its performance in applications like HBRV measurement.

According to another example embodiment the R peak detection unit may be switched off in cases there is no need for an accurate a reliable R peak detection and location. The system, for example, can be switched to a power efficient beat detection mode which can be used for the average HBR measurement, or can be switched to the highly efficient R peak search mode which can be used for the cases like HBRV measurements.

According to another example embodiment, the CWT computation around the valid beat advantageously reduces the CWT computations to be performed and requires less memory usage compared to the other techniques where the CWT computation is performed over the whole data.

According to another example embodiment, the R peaks can be detected within the hundreds of milliseconds after its occurrence, thereby making the technique implementable for real time applications, as well as for the applications where there is need to trace the R peaks immediately.

According to another example embodiment, the delay with the detection of the R peak of the ECG after its occurrence is calculated for the different algorithms. The block based CWT approach limits its immediate detection of the R peak while with the band power based algorithm it is confined within the hundreds of milliseconds proving it to be efficient for the systems where there is need of immediate detection of the R peaks.

Advantageously, the valid beat detection calculation according to an example embodiment of the disclosure is used for the extraction of the coarse features of the ECG signal. This technique is computationally very simple and hence consumes very low power. As a result a reduced amount of information is needed to be analyzed in order to extract the specific details from the ECG signal.

Also advantageously according to an example embodiment of the disclosure, the R peak detection and location technique presents higher performance and thus can extract the specific features from the ECG information set very accurately. The use of a high performance fine technique over a reduced set of information reduces the number of computations and consequently power dissipation.

According to another example embodiment, a low power system is provided. The low power system is configured for monitoring dynamically changing biopotential electrical signals, such as the ambulatory monitoring of Electrocardiogram (ECG). The low power system (power efficient) may be designed with the use of a dedicated analog signal processing ASIC (ASP), combined with a signal processing algorithm. The low power ASP system may comprise the following features: at least one electrode attached to the body of a biological sample, said electrode being arranged for measuring biopotential electrical signal; a high-performance chopped instrumentation amplifier configured for amplifying the received biopotential electrical signals; a time multiplexed analog to Digital Converter (ADC) arranged for receiving said biopotential electrical signals ECG and generating a digital output; at least one power efficient configurable analog band pass filter configured for outputting in-phase and quadrature components at a specified or target frequency band; at least one configuration register for configuring said configurable filter, wherein said configuration registers are arranged for configuring said ASP ASIC for providing a band power output signal at said specific frequency band. According to one example embodiment, the low power ASP system presented herein can be implemented a multi-channel device, where measurements are acquired from a plurality of electrodes. The ECG signals (biopotential electrical signal) received are processed by the ASP. The received signal, once processed, is analyzed with the help of a signal processing algorithm implemented on a low power microcontroller which can be optimized to take maximum advantage of the analog preprocessing capabilities of the ASP. The use of the heterodyne chopper readout is selected as the power efficient and configurable implementation of band pass filter. The ECG signal is first modulated and then is demodulated with an offset frequency that defines the center of the band pass filter. The width of the band pass filter is defined by the switched capacitor low pass filter after the demodulators. Configuration registers allow the setting of the offset frequency for the demodulator (center frequency of band pass filter) and the cut off frequency of the switched capacitor low pass filter (bandwidth of the band pass filter).

According to another example embodiment, a method is proposed for performing the beat detection and R peak search on an ECG signal received. A proposed algorithm is embedded in the ASP ASIC for evaluating the biopotential electrical signals (ECG) received. Advantageously, the method described satisfies the memory and computational complexity requirements of low power embedded systems used in portable applications. This can be achieved by combining a coarse algorithm (low power) and a fine algorithm (high performance) to extract the R peak from the ECG signal.

According to another example embodiment, the low power system may combine a coarse algorithm that detects the features of an EEG signal and a fine algorithm that refines the detection of the specific features in the coarse detection. The coarse and fine algorithms are applied to a specific portion of the ECG signal around the time window where the heart beat occurred. The combination of a coarse algorithm and a fine algorithm for monitoring and detecting the biopotential electrical offer the advantages of low power, high accuracy and faster response times. As an example the following two algorithms can be combined for the monitoring and detection of ECG signals: a beat detection algorithm for the detection of the QRS complex of ECG (coarse algorithm), and a continuous wavelet transform (CWT) algorithm over the detected QRS region then after for the detection of the R peak of the ECG (fine algorithm). The system may be able to switch between the two algorithms depending on the requirements of the application, for example between the low powered beat detection (coarse algorithm) and the high performance R peak detection algorithm (fine algorithm). The method does not exclude the combination of any other algorithms for meeting the specifications of a portable monitoring system.

According to another example embodiment, there is provided a method for monitoring biopotential electrical (ECG) signals. A method of monitoring ECG signals, wherein the step of extracting the band power of ECG is performed using the dedicated ASIC. A method of monitoring ECG signal, wherein the step of calculating the band power is performed by summing the squares of the magnitude of the in-phase and quadrature components. A method of monitoring ECG signals, wherein the step of calculating the adaptive threshold is calculated based on the 1 Hz low pass filtered version of the band power magnitude limited to the minimum of 18% of the moving averaged peak values. A method of monitoring the ECG signals, wherein the step of applying the highly accurate CWT method is performed in a selected region of the ECG signals received, preferably around the narrow detected beat (QRS complex of ECG) region instead of the whole ECG signal to save power by applying less computations with higher accuracy.

According to another example embodiment, there is provided a method for detecting dynamically changing biopotential electrical signals (ECG), such as heart beat detection. The method comprises the steps of: comparing the total band power exerted by the Low Power ASP with an adaptive threshold voltage (V2) for indicating the presence of the QRS complex; calculating the duration wherein said adaptive threshold is exceeded by the total band power, said duration being used as an additional constraint for checking the presence of a heartbeat; and recalculating said adaptive threshold, for the case where no occurrence of the QRS complex being detected during a predefined time. A method of detecting the presence of a heartbeat, wherein the QRS complex detected for duration longer than a predefined value is considered as a valid beat. A method of detecting the presence of a heartbeat, wherein the QRS complex detected for duration shorter than a predefined value is not considered a valid beat and is stored in the memory of the system. A method of detecting the presence of a heartbeat, wherein the QRS complex (heart beat) with the highest band power out of the plurality of heart beats stored in the memory of the system is chosen as a valid beat in the case where a valid beat is not detected within a predefined time.

According to another example embodiment, a method of detecting the R peak of a valid heart beat is provided, the method comprising the steps of: calculating the CWT of a portion of the received ECG signal, wherein said portion of the ECG signals selected to be around the detected valid beat; performing time domain search for locating the R peak of the valid beat detected. A method of detecting the R peak of a valid heart beat comprising the steps of: DC removal from the window (~140 ms) of an ECG signal around the detected QRS region; a CWT computation of that particular window of the ECG; and finding the maximum CWT coefficient. The maximum value of the CWT coefficient is calculated after the CWT computation is performed on the time window (around 140 ms) of the ECG signal (after DC removal), which is located around the detected valid beat, said maximum CWT coefficient is compared with 30% of the moving average of previous maximum coefficients stored in the system memory to determine a valid R peak. A method of detecting the R peak of a valid heart beat wherein time domain search is performed around the maximum CWT coefficients in a narrow window of the received ECG signals (around 20 ms) for locating the R peak position.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A microprocessor configured to receive and process digitized signals derived from an analogue ECG signal, said digitized signals being a digital ECG signal and digital in-phase and quadrature phase band power signals, the microprocessor comprising:
   a beat detection unit configured to receive the in-phase and quadrature phase band power signals, calculate a band power value and an adaptive threshold value, and compare said band power value with said adaptive threshold value to detect a QRS complex of the ECG signal indicative of a detected valid beat; and an R peak detection unit configured to receive the digital ECG signal and information about the detected valid beat, select a portion of the received ECG signal as a first time window around the detected valid beat; determine the location of a first R peak position based on a continuous wavelet transform calculation of said selected portion of the received ECG signal; and perform a time domain search in a second time window around said first R peak position in order to locate a final R peak position.

2. The microprocessor of claim 1, wherein the beat detection unit is further configured to measure the time period in which the band power value exceeds the adaptive threshold value, and, in case said measured time period is equal or greater than a first period of time, indicating said detected QRS complex as a valid beat, or in case said measured time period is less than the first period of time, said detected QRS complex is not considered as a valid beat and is stored in a memory.

3. The microprocessor of claim 1, wherein in case the beat detection unit does not detect, since the last detected valid beat, the occurrence of a new valid beat within a second period of time, it determines one, from a plurality of stored QRS complex, with the highest band power during the period and indicates said QRS complex as the valid beat.

4. The microprocessor of claim 1, wherein in case the beat detection unit does not detect, since the last detected valid beat, the occurrence of a new valid beat within a third period of time, the beat detection unit recalculates the adaptive threshold value.

5. The microprocessor of claim 2, wherein the first period of time is 32 milliseconds.

6. The microprocessor of claim 3, wherein the second period of time is an average beat duration time plus 200 milliseconds.

7. The microprocessor of claim 4, wherein the third period of time is 4 seconds.

8. The microprocessor of claim 1, wherein said adaptive threshold value used to detect the QRS complex of the ECG signal is defined based on the 1 Hz low pass-filtered version of the calculated band power value, limited to a minimum value of 18% of the peak value, and calculated as a moving average of a given number of previously calculated thresholds.

9. The microprocessor of claim 1, wherein the first time window is 140 milliseconds.

10. The microprocessor of claim 1, wherein the second time window is 20 milliseconds.

11. The microprocessor of claim 1, wherein the continuous wavelet transform calculation is a unit scale continuous wavelet transform calculation.

12. The microprocessor of claim 1, wherein the R peak detection unit is configured to determine the location of the first R peak position by determining, after a boundary removal of a fourth time period, the coefficient with maximum value of the continuous wavelet transform calculation of said selected portion of the received ECG signal, and comparing said coefficient with a given percentage of the mean of previously calculated maximum coefficient values.

13. The microprocessor of claim 12, wherein the fourth time period is 10 milliseconds.

14. The microprocessor of claim 12, wherein the given percentage is 30%.

15. A system for the analysis of ECG signals comprising:
an analog signal processing circuit including an electrocardiogram readout channel unit configured to generate, from a received analogue ECG signal, a digitized ECG signal; and a band power extraction channel unit configured to generate, from the received analogue ECG signal, digital in-phase and quadrature phase band power signals; and the microprocessor configured to receive and process signals provided by the analog signal processing circuit according to claim 1.

\* \* \* \* \*